(12) United States Patent
Thangaraj et al.

(10) Patent No.: US 7,160,484 B2
(45) Date of Patent: *Jan. 9, 2007

(54) METHOD AND DEVICE FOR THE PRODUCTION OF AN AQUEOUS SOLUTION CONTAINING CHLORINE DIOXIDE

(75) Inventors: Appadurai Thangaraj, Colonia, NJ (US); Barry K. Speronello, Montgomery Township, NJ (US); Timothy D. Wildman, Monmouth Junction, NJ (US)

(73) Assignee: Engelhard Corporation, Iselin, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/760,065

(22) Filed: Jan. 12, 2001

(65) Prior Publication Data

US 2001/0012504 A1    Aug. 9, 2001

Related U.S. Application Data

(62) Division of application No. 09/306,035, filed on May 6, 1999, now Pat. No. 6,238,643, which is a division of application No. 08/965,911, filed on Nov. 7, 1997, now abandoned.

(51) Int. Cl.
    *C01B 11/02* (2006.01)
(52) U.S. Cl. ............ 252/187.23; 423/477; 252/187.21; 252/186.24; 252/186.25; 252/186.36; 252/186.37
(58) Field of Classification Search ........... 252/187.21, 252/187.23, 186.2, 186.24, 186.25, 186.36, 252/186.37; 423/477
See application file for complete search history.

(56) References Cited

U.S. PATENT DOCUMENTS 2,022,262 A    11/1935    White ............... 87/5

(Continued)

FOREIGN PATENT DOCUMENTS

CA       959 238        12/1974

(Continued)

OTHER PUBLICATIONS

Derwent Publications Ltd., London, GB, AN311227, XP-002092338, Jul. 5, 1995.

(Continued)

*Primary Examiner*—Ngoc-Yen Nguyen
(74) *Attorney, Agent, or Firm*—Raymond F. Keller

(57) ABSTRACT

The present invention is generally directed to a method of producing an aqueous solution of chlorine dioxide from the reaction of a metal chlorite and an acid forming component which do not react to produce chlorine dioxide in the substantial absence of water. The reactants are separated from liquid water by a membrane which allows the controlled passage of liquid water and/or water vapor into contact with the reactants. The chlorine dioxide thus generated passes out through the membrane into the liquid water to produce the desired aqueous solution. Aqueous solutions containing chlorine dioxide produced in this manner can be conveniently used for commercial and domestic cleaning operations such as in the food industry.

24 Claims, 1 Drawing Sheet

U.S. PATENT DOCUMENTS

| | | | |
|---|---|---|---|
| 2,071,091 A | 2/1937 | Taylor | 167/17 |
| 2,071,094 A | 2/1937 | Vincent | 167/17 |
| 2,323,593 A | 7/1943 | Hampel et al. | 423/477 |
| 2,482,891 A | 9/1949 | Aston | 252/187 |
| 3,591,515 A * | 7/1971 | Lovely | 252/186.22 |
| 4,547,381 A | 10/1985 | Mason et al. | 423/477 |
| 4,585,482 A | 4/1986 | Tice | 106/15.05 |
| 4,683,039 A | 7/1987 | Twardowski et al. | 210/638 |
| 4,923,753 A | 5/1990 | Walles et al. | 428/402.24 |
| 4,998,671 A | 3/1991 | Leifheit | 239/44 |
| 5,009,875 A | 4/1991 | Kelly et al. | 423/477 |
| 5,106,465 A | 4/1992 | Kaczus et al. | 204/98 |
| 5,126,070 A | 6/1992 | Leifheit et al. | 252/186.36 |
| 5,360,609 A | 11/1994 | Wellinghoff | 514/772.3 |
| 5,567,405 A | 10/1996 | Klatt et al. | 423/477 |
| 5,695,814 A | 12/1997 | Wellinghoff et al. | 427/213 |
| 5,705,092 A | 1/1998 | Wellinghoff et al. | 252/187.21 |
| 5,719,100 A | 2/1998 | Zahradnik et al. | 252/187.23 |
| 5,965,264 A * | 10/1999 | Barenberg et al. | 428/402 |
| 5,974,810 A | 11/1999 | Speronello | 62/66 |
| 6,132,748 A * | 10/2000 | Khanna et al. | 424/405 |

FOREIGN PATENT DOCUMENTS

| | | |
|---|---|---|
| CN | 1104610 * | 7/1995 |
| EP | 0 230 737 A | 8/1987 |
| EP | 0 423 817 A | 4/1991 |
| EP | 0 581 550 | 2/1994 |
| JP | 01 071 804 | 3/1989 |
| WO | 98/388 865 | 9/1998 |

OTHER PUBLICATIONS

Derwent Publications Ltd., London, GB, AN90-079288, XP-002092128, Feb. 1, 1990.

Derwent Publications Ltd., Londong, GB, AN97-311277 (1997) no month.

* cited by examiner

METHOD AND DEVICE FOR THE PRODUCTION OF AN AQUEOUS SOLUTION CONTAINING CHLORINE DIOXIDE

This application is a division of application Ser. No. 09/306,035 filed May 6, 1999, now U.S. Pat. No. 6,238,643, which is a division of application Ser. No. 08/965,911 filed on Nov. 7, 1997, now abandoned.

FIELD OF THE INVENTION

The present invention is generally directed to a method of producing an aqueous solution of chlorine dioxide from the reaction of a metal chlorite and an acid forming component which do not react to produce chlorine dioxide in the substantial absence of water. The reactants are separated from liquid water by a membrane which allows the controlled passage of liquid water and/or water vapor into contact with the reactants. The chlorine dioxide thus generated passes out through the membrane into the liquid water to produce the desired aqueous solution. Aqueous solutions containing chlorine dioxide produced in this manner can be conveniently used for commercial and domestic cleaning operations such as in the food industry.

BACKGROUND OF THE INVENTION

Chlorine dioxide in low concentrations (i.e. up to 1,000 ppm) has long been recognized as useful for the treatment of odors and microbes. Its use is particularly advantageous where microbes and/or organic odorants are sought to be controlled on and around foodstuffs, as chlorine dioxide functions without the formation of undesirable side products such as chloramines or chlorinated organic compounds that can be produced when elemental chlorine is utilized for the same or similar purposes. For example, if a low concentration of chlorine dioxide gas can be maintained in contact with fresh produce for several days during shipping from the farm to the local retailer, the rate of spoilage of the produce can be decreased. In addition, chlorine dioxide gas is also generally considered to be safe for human contact at the low concentrations that are effective for deodorization and most antimicrobial applications.

Chlorine dioxide can be explosive at concentrations above about 0.1 atmosphere. Therefore, chlorine dioxide gas is not manufactured and shipped under pressure like other industrial gases, and conventional methods of on-site manufacture require not only expensive generation equipment but also high levels of operator skill to avoid generating dangerously high concentrations. These problems have substantially limited the use of chlorine dioxide to large commercial applications, such as pulp and paper bleaching, water treatment, and poultry processing, where the consumption of chlorine dioxide is sufficiently large that it can justify the capital and operating costs of expensive equipment and skilled operators for on-site manufacture.

Commercially, chlorine dioxide is produced from a variety of aqueous solutions of certain chlorine-containing salts, as disclosed for example in U.S. Pat. No. 5,009,875.

Attempts have also been made to produce chlorine dioxide using mixtures of solid reagents. Generally, the prior art has focused on three systems for chlorine dioxide production using solid reagents. One system employs a solid mixture of a metal chlorite and an acid in a liquid, aqueous environment. A second system combines a metal chlorite and a solid acid where chlorine dioxide gas is released under dry conditions. A third system employs the combination of a metal chlorite and a solid organic anhydride to generate a high concentrated flow of chlorine dioxide which must be diluted with a constantly flowing stream of inert gas.

Each of these solid reagent systems is disadvantageous for any one or more of the following reasons:

a) upon mixing there is normally a sudden, highly concentrated stream of chlorine dioxide generated;

b) the mixture of reactants produces chlorine dioxide gas under dry conditions thereby reducing the shelf life of the reactants; and c) an inert gas stream must be used to reduce the concentration of chlorine dioxide gas in the atmosphere.

Aqueous solutions of chlorine dioxide are also known in the art. Two types of synthesis processes are generally used to provide chlorine dioxide solutions for commercial uses, such as poultry chiller water purification, washwater purification, potable water treatment and as a teat dip for the control of non-human mammalian mastitis.

The first type of synthesis process is based on the manual combination of two aqueous solutions; one containing a source of chlorite anions and another being acidic. The solution containing chlorite anions is usually a solution of sodium chlorite having a concentration of between about 100 ppm and about 5% by weight and having a pH of about 13. The acidic solution may contain any acid capable of providing a pH below about 8.5 after the solutions are mixed. Such acids include citric acid, lactic acid, hydrochloric acid, sulfuric acid, and dissolved carbon dioxide (i.e., sodium bicarbonate). The antimicrobial performance of the resultant solutions depends upon the degree to which the chlorite anions from the chlorite source solution are converted to free molecular chlorine dioxide ("Chlorine Dioxide") in the solution, as Chlorine Dioxide is the effective agent for both antimicrobial and deodorization activity.

In one variation on this synthesis process the pH of the sodium chlorite solution is reduced from about 13 to about 8 using the acidic solution. Chlorite anion is thus converted to Chlorine Dioxide via the reaction below.

Such solutions having a pH of about 8 are generally referred to in the industry as "stabilized" chlorine dioxide solutions, and usually contain between about 100 ppm and 5% of a mixed solution of Chlorine Dioxide and unconverted chlorite anion. Because the acid concentration is relatively low at a pH of 8, the typical ratio of Chlorine Dioxide to chlorite anion in a stabilized chlorine dioxide solution is less than 0.01. Therefore, for a given initial concentration of chlorite anion, stabilized chlorine dioxide solutions are relatively weak antimicrobial agents due to their low conversion of chlorite anion to Chlorine Dioxide. Also, since they are typically supplied at a concentration of less than about 5% by weight sodium chlorite, they are relatively expensive to ship and store due to the high weight of water that must be transported as part of the solution.

Chlorite anion is generally stable in stabilized solutions (pH 8), so they have an advantageously long shelf life. To improve their effectiveness, however, they are typically activated just prior to use by the addition of a strong acid to lower their pH to below about 3.5 and convert more chlorite anion to Chlorine Dioxide via the reaction shown above. Since the activation process involves the addition of a strong acid to lower the pH, it requires a high level of operator skill to handle, measure and mix the acid with the stabilized chlorine dioxide solution. Also, since the activation process results in a solution having a pH of less than about 3.5, such activated solutions are not well suited to work in combination with, for example, detergents which work best under alkaline or neutral pH conditions. Contact of these solutions with many metals should also be limited because of possible metallic corrosion by the acidic solution.

Such activated solutions typically have a ratio of Chlorine Dioxide to chlorite anion below about 0.05 when the solution is acidified to a pH of about 3. It is possible to achieve a higher ratio of Chlorine Dioxide to chlorite anion in such activated solutions, but doing so is dangerous and requires extreme operator skill. Achieving a ratio of Chlorine Dioxide to chlorite anion above about 0.05 requires further acidification to a much lower pH than 3 (typically less than 2) and often requires that the further acidification be performed at concentrations of chlorite anion above about 5000 ppm. Under such conditions of extremely low pH and high chlorite ion concentration it is possible to generate a sufficient chlorine dioxide concentration in solution such that the vapor pressure of gaseous chlorine dioxide in equilibrium with the solution approaches the explosive range. Therefore, it is not common practice to produce solutions having a high ratio of Chlorine Dioxide to chlorite anion by manual acidification (i.e. without chlorine dioxide generation equipment as discussed below).

In the second type of chlorine dioxide solution synthesis process, chlorine dioxide solution is generated from either a sodium chlorite solution or stabilized chlorine dioxide solution using chlorine dioxide generation equipment at the point of use. The generated solution typically has a ratio of Chlorine Dioxide to chlorite anion of between about 10 and 25, and as a result such solutions are highly effective antimicrobial agents. Since generated chlorine dioxide solution is typically used shortly after generation, the relatively high decomposition rate of chlorine dioxide in solution is unimportant. Also, since aqueous sodium chlorite is commercially available at higher concentrations than are typically available in the form of stabilized chlorine dioxide solutions, the cost of storing and shipping the aqueous sodium chlorite solutions can be lower when compared to stabilized chlorine dioxide solution. However, the high cost of the chlorine dioxide generation equipment and the high level of operator skill needed for its operation makes generated chlorine dioxide solution best suited to relatively large applications such as water treatment and poultry processing where the consumption of chlorine dioxide is sufficiently large that it can justify the capital and operating costs.

In addition to the two types of commercial synthesis processes for chlorine dioxide solution discussed above, it is also possible to generate solutions containing chlorine dioxide and having a high ratio of Chlorine Dioxide to chlorite anion by absorption of gaseous chlorine dioxide into water. Chlorine dioxide is first produced in solution by conventional means, e.g. acid activation of a solution of sodium chlorite. Inert carrier gas, typically air or nitrogen is then bubbled through the activated solution where it picks up some of the Chlorine Dioxide. That gaseous mixture of Chlorine Dioxide and carrier gas is then bubbled through a second vessel containing water where the Chlorine Dioxide is dissolved to produce a solution of chlorine dioxide typically having a ratio of Chlorine Dioxide to chlorite anion between about 20 and about 50. While it is possible to produce substantially pure solutions of chlorine dioxide in this manner, it requires a very high level of operator skill and is rarely done outside of the laboratory.

Attempts have been made to reduce the cost of generating chlorine dioxide solutions by using mixtures of alkaline chlorite salts and acidic dry powders which, upon addition to water, acidify the water and generate chlorine dioxide via reaction described above. U.S. Pat. No. 2,022,262, discloses stable stain removing compositions comprising a dry mixture of a water soluble alkaline chlorite salt, an oxalate, and an acid. Since alkaline chlorites are strong oxidizers and corrosively caustic, a relatively high level of user skill is needed to employ this process. Furthermore, the pH of the resultant solution is acidic, so such acidic solutions of chlorine dioxide are not well suited for use in combination with detergents which work best under alkaline or neutral conditions. Finally, the resultant solution contains contaminants including sodium chloride, and the solution byproducts of the oxalate and acid as contaminants.

U.S. Pat. No. 2,071,091 discloses an improved fungicide and bactericide, and an improved sterilization process using chlorous acid and the salts of chlorous acid. The term "chlorous acid and the salts of chlorous acid" includes aqueous solutions of soluble chlorite salts that have been acidified to an acidic pH. Such solutions contain mixtures of chlorine dioxide and chlorite anions with the ratio of Chlorine Dioxide to chlorite being higher when the pH of the solution is lower. As with the '262 Patent discussed above, this process requires a relatively high degree of user skill to handle and measure the alkaline chlorite and acid. The requirement for an acidic pH limits the utility of this process when the preferred solution pH is alkaline, and the resultant solution is contaminated with sodium chloride and the solution byproducts of the acid.

U.S. Pat. No. 2,071,094 discloses deodorizing compositions in the form of dry briquettes comprising a dry mixture of a soluble chlorite, an acidifying agent and a filler of lower solubility. Generation of chlorine dioxide begins as the briquette dissolves in water. This process is suitable for unskilled users, but still requires that the resultant solution be produced at an acidic pH, and it is still contaminated with the solution byproducts of the reagents. Furthermore, the inert, low solubility filler leaves an insoluble residue paste that is difficult to handle and dispose of.

U.S. Pat. No. 2,482,891 discloses stable, solid, substantially anhydrous compositions comprising alkaline chlorite salts and organic acid anhydrides which release chlorine dioxide when contacted with water. The patent disclosure indicates that the preferred solution is highly concentrated and consequently would have been at an acidic pH. As such, this process suffers from the same limitations as the '262 and '091 Patents mentioned above.

U.S. Pat. No. 4,585,482 discloses a long-acting biocidal composition comprising a chlorine dioxide liberating compound and a hydrolyzable organic acid-generating polymer. Methods are disclosed for producing dry polymer encapsulated microcapsules containing such compositions and water such that the resultant dry materials release chlorine dioxide gas. The primary purpose of the polymer encapsulating film of the '482 Patent is to provide for hard, free flowing particles, and to protect against the loss of water from the interior of the microcapsule. If the micro capsules were to be immersed in water, they would produce a chlorine dioxide solution. Producing chlorine dioxide solution in this manner would eliminate the complications of measuring and mixing reagents and the cost of capital equipment that characterize the prior art. In addition, the solution pH need not be acidic so it would be feasible to produce chlorine dioxide in a detergent solution. However, the materials of the '482 Patent are not storage stable because they begin to release chlorine dioxide as soon as they are manufactured. Furthermore, they release chlorine dioxide over a period of several days, so they are unsuitable for quickly preparing a useable chlorine dioxide solution. Finally, once mixed in water the microcapsules cannot be removed from the water in a simple fashion. Typically they must be separated by a process such as filtration.

It would therefore be a significant advance in the art of preparing aqueous solutions containing chlorine dioxide for commercial applications, especially small to medium size applications (e.g. ones requiring from 1 mg to 500 gm of chlorine dioxide per day) to have a method whereby chlorine dioxide containing solution may be prepared in a simple manner without the need for measuring and mixing of corrosive chemicals. It would be a further advance in the art for said method to produce solutions having a ratio of Chlorine Dioxide to chlorite anion above about 0.05, preferably at any pH between about 2 and 10. It would also be a further advance in the art to provide a device for containing the reactants needed to generate chlorine dioxide and to be able to place the device into a body of water when needed to produce an aqueous solution containing chlorine dioxide on demand, preferably without the introduction of contaminants into the body of water.

SUMMARY OF THE INVENTION

The present invention is generally directed to a method and device for producing an aqueous solution containing chlorine dioxide. In a particular aspect of the present invention, the device, which contains selected amount of reactants for producing chlorine dioxide, is added to a measured body of water and while present therein allows the controlled passage of liquid water and/or water vapor into the device so as to initiate a reaction which generates a predetermined amount of chlorine dioxide. The chlorine dioxide is then able to pass out through the device into the body of water so as to form an aqueous solution containing the desired concentration of chlorine dioxide.

In particular, the present invention is directed, in part, to a method of producing an aqueous solution containing chlorine dioxide comprising:

a) having liquid water in a first zone and at least one metal chlorite and at least one acid forming component in a second zone, said first and second zones being separated by a membrane;

b) contacting said membrane with water from said first zone such that liquid water and/or water vapor passes through said membrane into said second zone thereby facilitating the reaction between said at least one acid forming component and said at least one metal chlorite to produce chlorine dioxide; and c) allowing the chlorine dioxide produced in the second zone to pass out through said membrane to the first zone into the liquid water to form said aqueous solution.

The present invention is also directed to a device which generates chlorine dioxide in the presence of water but not in the substantial absence of water. In a preferred aspect, said device, when placed in liquid water, may be used to generate an aqueous solution containing chlorine dioxide on demand. In particular, the device comprises a membrane defining, at least in part, an enclosed space, said enclosed space containing at least one metal chlorite and at least one acid forming component. The membrane is made of a material which permits: (a) liquid water and/or water vapor to pass therethrough into the enclosed space to allow the at least one metal chlorite and at least one acid forming component to react to produce chlorine dioxide and (b) the so produced chlorine dioxide to pass therethrough out into the liquid water to produce the product solution containing chlorine dioxide.

The present invention can be adapted to provide the controlled release of chlorine dioxide by employing reactants and membranes which readily dissolve in water ("Embodiment A") or by employing membranes and optionally reactants which are more resistant to dissolution ("Embodiment B").

In Embodiment A, the resultant chlorine dioxide containing solution comprises chlorine dioxide, solubilized membrane, and the soluble byproducts of the reaction between the metal chlorite and the acid forming component. In this embodiment, separation, handling and disposition of undissolved solid waste products is substantially eliminated because the device and its contents substantially dissolve in the product chlorine dioxide containing solution. However, the product solution will contain small amounts of dissolved impurities (e.g. typically less than 1000 ppm) as discussed above.

In Embodiment B, the at least one metal chlorite and at least one acid forming component are initially separated from the liquid water by a membrane which does not substantially dissolve during the generation of chlorine dioxide. This embodiment produces chlorine dioxide solutions of higher purity than Embodiment A because at least a portion of the reaction byproducts from the reaction between the metal chlorite and acid forming component are substantially retained by the membrane which is at least substantially insoluble and therefore the byproducts do not enter the product aqueous solution containing chlorine dioxide in appreciable quantities.

For purposes of the invention, Embodiments A and B are preferred, however, the invention also contemplates that substantially insoluble reactants may be used with substantially soluble membranes and substantially soluble reactants may be used with substantially insoluble membranes and that mixtures of insoluble and soluble reactants may be used with either type of membrane.

BRIEF DESCRIPTION OF THE DRAWINGS

The following drawings are illustrative of embodiments of the invention and are not intended to limit the invention as encompassed by the claims forming part of the Application.

DETAILED DESCRIPTION OF THE INVENTION

The present invention is directed to a method for generating an aqueous solution of chlorine dioxide and a device which may be used to carry out the method. In accordance with one aspect of the present invention, solid reactants which react with each other in the presence of water but not in the substantial absence of water to produce chlorine dioxide, are separated from a body of water by a membrane. The membrane allows the controlled passage of liquid water and/or water vapor through the membrane into contact with the reactants to produce chlorine dioxide and then allows the passage of the chlorine dioxide out through the membrane into the body of water to produce an aqueous solution containing chlorine dioxide.

The solubility in water of the reactants and especially the permeability and solubility of the membrane can be selected to increase or decrease the purity of the resulting aqueous solution of chlorine dioxide and the ease of handling and disposal of the device and byproducts.

Figure 1:
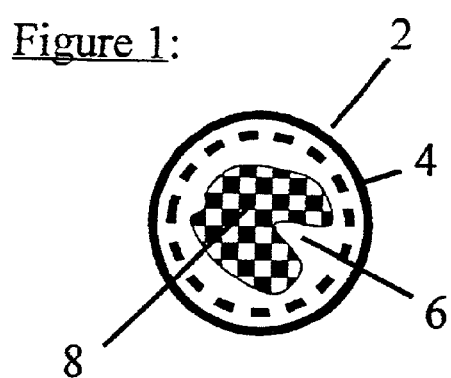
FIG. 1 is a device contemplated by the invention for generating chlorine dioxide.
Figure 2:
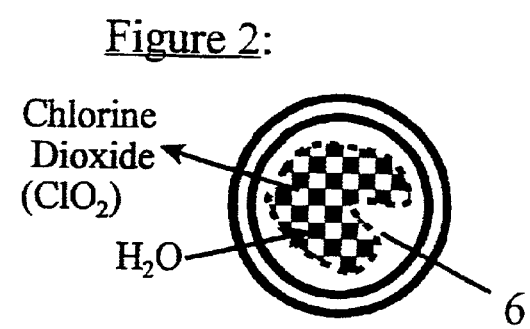
FIG. 2 is a cross-sectional view of the device shown in FIG. 1.
Figure 4:
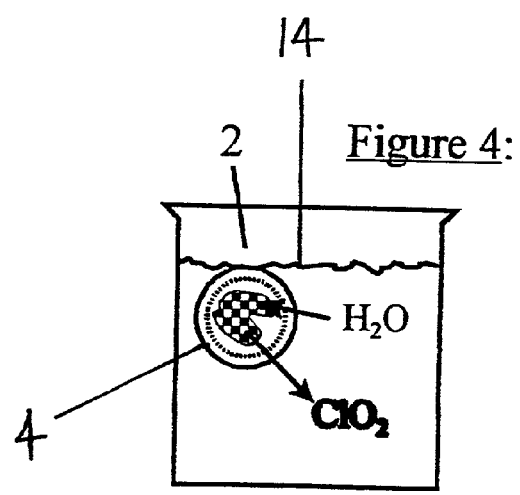
FIG. 4 is a view of the device of the invention shown in FIG. 1 within a body of water.

Referring to FIGS. 1, 2, and 4, there is shown an embodiment of a device 2 of the present invention which contains reactants 8 within an enclosed space 6 which is surrounded by an enclosure that is comprised at least in part by a membrane 4. The device 2 includes a membrane 4 which allows water in the form of liquid and/or vapor to pass therethrough from a body of liquid water 14. As shown in FIG. 4, the membrane 4 also allows the passage of chlorine dioxide therethrough into the body of water 14 so as to form the solution containing chlorine dioxide.

As shown in FIG. 1, the membrane 4 at least in part defines an enclosed space 6 which contains the reactants 8 needed to generate chlorine dioxide. Generally the reactants 8 comprise a metal chlorite and an acid forming component as more specifically defined hereinafter.

The membrane 4 allows the controlled passage of water from the body of water 14. Once sufficient water has entered the enclosed space 6 through the membrane 4 the reactants 8 produce chlorine dioxide. The chlorine dioxide then passes out through the membrane 4 into the body of water 14.

Figure 3:
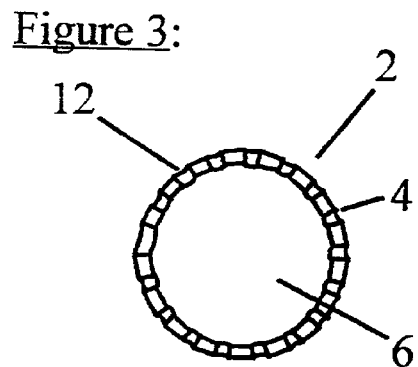
FIG. 3 is a cross-sectional view of a second embodiment of a membrane for use in the device of the invention.

The membrane 4 is water permeable and thereby enables water to pass into the enclosed space 6 of the device 2. As shown in FIG. 3, the membrane 4 may be provided with micropores 12 of sufficient dimensions to allow water to pass into the device 2 and also allow chlorine dioxide to pass out of the device 2. The membrane 4 may initially be low in porosity or nonporous, and later during the course of the reaction develop additional porosity which can facilitate the passage of chlorine dioxide out into the body of water 14.

In a preferred form of the invention, the device 2 can be constructed with selected amounts of reactants 8 so as to generate an aqueous solution having a desirable concentration of chlorine dioxide for a suitable purpose. In use, the device 2 is contacted with a selected amount of water. In a controllable amount of time, the selected amount of water in the vessel receives a predetermined amount of chlorine dioxide based on the amount of reactants present to form an aqueous solution containing the desired concentration of chlorine dioxide.

The selection of the reactants (at least one metal chlorite and the at least one acid forming component) as well as the membrane material depends in part on the relative importance of several factors to the particular end use of the chlorine dioxide containing solution. The factors include: the reaction rate (i.e. the rate of generation of chlorine dioxide), the desired purity of the resulting aqueous solution containing chlorine dioxide, and the ease of handling and disposal of the reaction waste products. If reaction rate is of primary importance, then it is preferred to select reactants which are more water soluble and membrane materials which are more permeable to both water and chlorine dioxide. If purity of the resultant product solution is of primary importance, then it is preferred to select reactants which produce byproducts which are not substantially water soluble and membrane materials which are also not substantially water soluble. If elimination or reduction of waste product handling and disposal is of primary importance, then it is preferred to select membrane materials and reactants whose byproducts are substantially water soluble.

The selection of water soluble reactants facilitates rapid dissolution and reaction of the reactants to produce chlorine dioxide in the presence of liquid water. A more highly permeable membrane material allows more rapid transfer of water in through the membrane and rapid transfer of the thus produced chlorine dioxide out into the body of water to form the desired solution. If desired, reactants can be chosen so that all of the byproducts are substantially water soluble. If a water soluble membrane is also chosen, then the aqueous solution containing chlorine dioxide does not have to be further processed to remove either membrane residue or the insoluble byproducts of the reactants, i.e. Embodiment A.

A membrane material which is not substantially soluble is preferred when it is desired to limit the introduction of species other than chlorine dioxide into the product solution. The purity of the aqueous solution can be further enhanced by incorporating into the enclosed space containing the reactants one or more materials which form an insoluble phase with at least one otherwise soluble reaction byproduct. As a result, the at least one otherwise soluble reaction byproduct cannot escape out through the membrane into the aqueous solution containing chlorine dioxide because the at least one otherwise soluble reaction byproduct is tied up in at least one insoluble phase.

The metal chlorites employed in the present invention can generally be any metal chlorite as well as mixtures thereof. Preferred metal chlorites are water soluble and include alkali metal chlorites, such as sodium chlorite and potassium chlorite as well as alkaline earth metal chlorites. Examples of alkaline earth metal chlorites include barium chlorite, calcium chlorite, and magnesium chlorite. The most preferred metal chlorite is sodium chlorite, especially dry technical grade sodium chlorite containing about 80% by weight of sodium chlorite and 20% by weight of sodium chloride.

The acid forming component is preferably a dry solid hydrophilic material which does not react substantially with the metal chlorite during dry storage. The acid forming component does, however, react with the metal chlorite to form chlorine dioxide when in the presence of liquid water and/or water vapor. As used herein the term "acid forming component" shall mean a dry solid hydrophillic material which is itself acidic or produces an acidic environment when in contact with liquid water and/or water vapor and metal chlorite. The acid forming component may be water soluble or substantially insoluble in water. The preferred acid forming components are those which produce a pH of below about 7, more preferably below about 5 when the aqueous portion of a concentrated mixture of the solid in deionized water is measured.

Examples of preferred substantially water soluble acid forming components include, but are not limited to, water soluble solid acids such as boric acid, citric acid, tartaric acid, water soluble organic acid anhydrides such as maleic anhydride, and water soluble acid salts such as calcium chloride, magnesium chloride, magnesium nitrate, lithium chloride, magnesium sulfate, aluminum sulfate, sodium acid sulfate ($NaHSO_4$), sodium dihydrogen phosphate ($NaH_2PO_4$), potassium acid sulfate ($KHSO_4$), potassium dihydrogen phosphate ($KH_2PO_4$), and mixtures thereof. The most preferred acid forming component is sodium acid sulfate. Additional water soluble acid forming components will be known to those skilled in the art and are included within the scope of the present invention.

Examples of preferred substantially water insoluble acid forming components include, but are not limited to, synthetic molecular sieves such as synthetic zeolite Y, dealuminated zeolite Y, mordenite and ZSM-5 which have been converted to the substantially hydrogen ion ($H^+$) exchanged forms; acid ion exchange resins such as Dowex™ HCR-S resins (sold by Dow Chemical Company); acid treated clays such as acid treated bentonite; and acid treated calcined clays such as acid treated spinel calcined kaolin and acid treated metakaolin, insoluble organic acid anhydrides such as phthalic anhydride, and mixtures thereof. The preferred substantially water insoluble acid forming component is acid treated metakaolin. Additional water insoluble acid forming components will be known to those skilled in the art and are included within the scope of the present invention.

As previously indicated, one or more materials which form an insoluble phase with at least one otherwise soluble reaction byproduct may be included with the reactants or may itself be a reactant. In a preferred embodiment an acid forming component can be used which is primarily present as a source of acidity, but which also reacts with cations which may be present to form an insoluble phase which is retained by the membrane. The practice of this embodiment permits the production of highly pure aqueous solutions containing chlorine dioxide. Such materials ("Ion Exchangers") are preferably solid, water insoluble $H^+$ ion exchangers having a high selectivity for cations in the reactants and reaction byproducts, e.g. cations of the metal chlorite. The Ion Exchangers capture the cations by ion exchange with $H^+$. The predominant resultant soluble reaction product is therefore only chlorine dioxide with a possible trace amount of hydrogen chloride.

Examples of such Ion Exchangers include, but are not limited to, synthetic molecular sieves such as synthetic zeolite Y, dealuminated zeolite Y, mordenite and ZSM-5 which have been converted to the substantially $H^+$ exchange forms; acid ion exchange resins such as Dowex™ HCR-S resins (sold by Dow Chemical Company), as well as mixtures thereof. The preferred Ion Exchanger for this embodiment of the invention is the acid form of synthetic zeolite Y. Additional Ion Exchangers will be known to those skilled in the art and are included within the scope of the present invention.

Ion Exchangers are not the only materials suitable for forming insoluble phases by reacting with otherwise soluble phases. For example, when ionic calcium is an otherwise soluble phase, it is useful to include constituents comprising soluble sulfate and/or phosphate anions in the enclosed space with the reactants. Sulfate and phosphate anions will react with ionic calcium to form the insoluble phases calcium sulfate and calcium phosphate respectively, and consequently prevent the escape of the calcium out of the membrane into the product solution. The preferred phases containing sulfate and/or phosphate are the acid forming components sodium acid sulfate and sodium dihydrogen phosphate. Other combinations of materials that react with otherwise soluble phases to yield insoluble phases are known to those skilled in the art and are included within the scope of this invention.

The amounts of the metal chlorite and the acid forming component used must be sufficient to generate a quantity of chlorine dioxide sufficient to combine with the body of water to form an aqueous solution containing the desired concentration of chlorine dioxide. Generally, aqueous chlorine dioxide solutions useful for disinfecting purposes contain from about 0.5 to about 200 ppm of chlorine dioxide. If, for example, a liter of solution containing about 100 ppm of chlorine dioxide were desired, the required amount of the metal chlorite, specifically sodium chlorite, would be about 170 mg. The amount of acid forming component should be sufficient to provide an excess of acid beyond that needed to neutralize the alkalinity of the metal chlorite and the incoming water. Preferably the amount of the acid forming component should be sufficient to maintain a pH of less than about 5 and more preferably less than about 3.5 when in contact with the metal chlorite. Calculation of the amount of metal chlorite, specifically sodium chlorite, can be imputed by methods well known in the art based on the reaction:

$$5NaClO_2 + 5H^+ \leftrightarrows 4ClO_2 + HCl + 2H_2O + 5Na^+$$

Other constituents may be included within the enclosed space in addition to the reactants and phases that form insoluble phases with otherwise soluble phases. For example, desiccant materials may be included to increase the storage stability of the reactants by protecting them from humidity (which can cause humidity induced premature reaction to form chlorine dioxide). Deliquescent materials may also be included in the enclosed space to accelerate the onset of the chlorine dioxide forming reaction once the membrane is contacted with water. Deliquescent materials absorb water vapor and convert it to liquid water. Consequently, soluble reactants can dissolve and begin rapidly to react to form chlorine dioxide even before liquid water has penetrated the membrane. Calcium chloride is both the preferred desiccant material and preferred deliquescent material. Additional materials having these characteristics will be known to those skilled in the art and are included within the scope of the present invention.

The solid metal chlorite and the solid acid forming component can be in any physical form which can be contained within the device. The solid reactants can be in the form of powders, granules, pellets, tablets, agglomerates and the like. In a preferred aspect of the invention, one or both of the reactants are present in the form of relatively large agglomerates (as defined below).

In this preferred aspect of the invention the agglomerates do not contain mixtures of metal chlorites and acid forming components. Thus one type of agglomerate contains only one or more metal chlorites or a mixture of metal chlorite(s) and one or more non-acid forming additive(s) (e.g. silica gel desiccant, paraffin wax tableting binder, and/or sodium sulfate filler). The second type of agglomerates are substantially free of the metal chlorite, and at least one type of them comprises the acid forming component as defined herein, and may also contain one or more metal chlorite-free additives (e.g. Ion Exchangers, tableting binders, and/or desiccants). In this preferred embodiment the preferred composition also does not contain constituents that deliquesce upon exposure to ambient humidity. This aspect is the preferred aspect when it is desired that the materials be resistant to premature conversion to chlorine dioxide as a result of ambient humidity (i.e. when it is desirable for the materials to react to form chlorine dioxide substantially only when they are exposed to liquid water).

Large agglomerates allow less costly packaging materials to be used for packaging of the device. Specifically, if powdered mixtures of reactants are exposed to high levels of ambient humidity for an extended period of time during storage, they will undergo humidity activated premature reaction to form chlorine dioxide. To prevent such premature reaction, powdered reactants can be packaged in humidity barrier materials such as foil pouches, glass bottles, and metal cans. Such packaging is expensive and its use can be reduced or eliminated if the physical form of the reactants inhibits them from undergoing excessive premature humidity activated reaction, i.e. if they are in the form of large agglomerates.

Applicants have discovered that when the particles of metal chlorite and the acid forming component have a particle size of up to about 80 microns in diameter they may react prematurely due to exposure to humidity. Larger particles, probably because of their reduced interfacial contact area, react more slowly upon exposure to humidity. Consequently, in a situation where humidity activated chlorine dioxide formation is undesirable, larger particles (i.e. $\geq 80$ microns) are preferred.

The term "relatively large agglomerates" as used herein shall mean agglomerates having a particle size of at least 80 microns preferably above about 100 microns (0.1 mm), more preferably above about 500 microns (0.5 mm), and most preferably above about 1,000 microns (1 mm). Such particles will exhibit a reduced rate of humidity activated chlorine dioxide release, but can dissolve and will readily react in contact with liquid water to produce chorine dioxide.

The membrane employed in the present device serves two functions. First, it must provide for the controlled passage of liquid water and/or water vapor from a source (typically the body of water that is to be treated to form an aqueous chlorine dioxide solution) into the device so that the metal chlorite and the acid forming component can react with each other within the enclosed space under acidic internal pH to produce chlorine dioxide. Second, the membrane must also allow the passage of chlorine dioxide out therethrough into the body of water.

As previously indicated, the membrane materials can be selected from substantially water soluble materials when ease of waste product handling is important and dissolved byproducts are acceptable. Substantially insoluble membrane materials are appropriate when it is desirable to avoid introducing species other than chlorine dioxide (such as soluble membrane constituents) to the product solution.

Preferred substantially water soluble membrane materials include gelatin, polyvinyl alcohol, cellulose, and derivatives of cellulose including but not limited to hydroxypropyl methyl cellulose. Additional substantially water soluble materials will be known to those skilled in the art and are included within the scope of the present invention.

The preferred substantially water soluble membrane materials such as gelatin are water softenable and will for the most part dissolve in water. As a result, the membrane material may become fully dissolved in the aqueous solution of chlorine dioxide and does not have to be removed therefrom after use.

The preferred substantially water soluble membrane material is gelatin preferably in the form of capsules such as Capsugel® brand manufactured by Warner Lambert Co. Such capsules are initially nonporous, but soften in contact with liquid water so that once the reaction to form chlorine dioxide has substantially commenced the membrane develops pores which facilitate the escape of chlorine dioxide into the liquid water to produce the product solution containing chlorine dioxide.

The preferred substantially insoluble membrane materials which provide a barrier to keep insoluble reactants and reaction byproducts from contaminating the aqueous solution containing chlorine dioxide are microporous nonwoven hydrophobic polymer sheet materials including nonwoven polyethylene (e.g. Tyvek® brand sold by Dupont) and expanded polytetrafluoroethylene (e.g. GoreTex® brand sold by W. L. Gore). Also preferred are membranes made of kraft paper such as X-Crepe-N Grade 4502 as supplied by Oliver Products Company, Grand Rapids Mich.

A more highly permeable membrane is desired when rapid reaction rate is important. High permeability allows for more rapid controlled infusion of water into the enclosed space containing the reactants and it facilitates escape of the chlorine dioxide into solution. It is important, however, that the permeability rate for water be sufficiently low so that sufficient internal acidity of the enclosed space is maintained in order for the reaction rate to be sustained, i.e. the acidity should not be excessively diluted by the too rapid passage of liquid water into and out of the membrane. In a preferred embodiment for rapid chlorine dioxide release the permeability rate of the membrane will result in the onset of chlorine dioxide release in about 5 minutes.

The preferred membrane materials for rapid release when ease of disposal is important is gelatin (preferably in the form of capsules). The preferred membrane materials for rapid release when solution purity is important are perforated Tyvek or perforated kraft paper (preferably in the shape of flat sachets or "tea bags"). The preferred size and density of the perforations will depend on several factors, including the size of the package, the depth of immersion in the body of water, the temperature of the water, and the wetting characteristics of the body of water. Fewer and smaller perforations are needed when depth, temperature, and wetting characteristics are greater. Good results can be achieved with perforations made with a conventional sewing needle and spaced between about 2 mm and 10 mm apart.

EXAMPLES

General Procedure for Sample Preparation and Estimation of Chlorine Dioxide and Chlorite Anion Concentrations in Solution Sodium chlorite (technical grade supplied by Energia E Industrias Aragonesas, S.A., Madrid, Spain) was dried at 95° C. for 2 hours and placed in a sealed container. Similarly, the acid forming components were dried separately at 200–500° C. for 3–5 hours and transferred into bottles and sealed. A physical mixture of dried reactants was formed by mixing the desired amounts of dried sodium chlorite and dried acid forming component in a glove bag under dry conditions (relative humidity typically below about 5%). The resultant physical mixture of dried reactants was stored under dry condition in a sealed glass jar.

Devices comprising a Tyvek membrane were made by heat sealing Tyvek brand nonwoven polyethylene fabric (type 1059B supplied by Dupont Corp.) into the form of a generally square pouch about 1.5 inches long on each side. Heat sealing was done with a conventional lab scale heat sealer designed to seal low density polyethylene films. Initially each pouch was sealed on three sides and the fourth side was left open to add reactants. A measured amount of a physical mixture of dried reactants was placed into a Tyvek pouch and the fourth side was heat sealed. The resultant device, referred to as a sachet, was then immersed in a known amount of deionized water in a closed glass bottle for a known amount of time to produce a solution containing chlorine dioxide.

The total oxidant concentration (i.e. Total Oxidant Concentration) in each solution containing chlorine dioxide was determined by standard Iodometric titration using the following procedure. One hundred (100) ml of solution containing chlorine dioxide was placed in 200 ml beaker and 2 grams of potassium iodide was added. After a minute of stirring, 15 ml of 1 N H$_2$SO$_4$ solution was added and stirred for 3 more minutes. The solution was then titrated with a 1 N solution of sodium thiosulfate using an auto titrator (Model 716 DMS Titrine, Brinkmann, Metrohm). The Total Oxidant Concentration is then calculated using the following equation:

TotalOxidantConcentration(mg/liter)=$A \times N \times 134.9$

Where, A=Volume of titrant (ml, thiosulfate)
N=Normality of thiosulfate (1N)

This procedure provides a measure of the total amount of chlorine dioxide oxidant capacity contained in the solution. This includes the sum of the chlorine dioxide present, plus the quantity of chlorine dioxide that would result from the conversion of any chlorite anion in the solution to chlorine dioxide by acid activation (i.e. 5 moles of chlorite yields 4 moles of chlorine dioxide).

The concentration of chlorite anion in solution (i.e. Chlorite Concentration) was determined as follows. One hundred (100) ml of solution containing chlorine dioxide was placed in an open glass jar and stripped of its chlorine dioxide by bubbling nitrogen through the solution at a flow rate of about 100 ml/min for about 1 hour until all traces of yellow color were eliminated. The resultant stripped solution was analyzed using the standard iodometric titration procedure as described above. This result is a measure of the equivalent concentration of chlorine dioxide that would be produced by acid activation of the chlorite anion in the solution (i.e "Chlorite Oxidant Concentration"). The actual chlorite anion concentration was calculated using the equation below:

ChloriteConcentration=1.25[ChloriteOxidantConcentration]

The concentration of free molecular chlorine dioxide in solution was calculated as the difference between the Total Oxidant Concentration, and the Chlorite Oxidant Concentration as measured in the tests above.

The sodium concentration in the chlorine dioxide solution was estimated by conventional atomic absorption spectroscopy (AAS) and on some samples of solutions the concentrations of $ClO_2^-$, $ClO_3^-$ and $Cl^-$ ions were estimated by ion chromatography using a procedure similar to US EPA test method 300.

Preparation of Standard Chlorine Dioxide Solution

Ten (10) grams of technical grade sodium chlorite was dissolved in 200 ml of deionized water and transferred into a first impinger bottle with a bubbler. The output of the first impinger bottle was connected with teflon tubing to the bubbler inlet of a second impinger bottle containing 200 ml of deionized water. An airflow of 10 cc/min was passed into the bubbler of the first impinger bottle, through the sodium chlorite solution, into the bubbler inlet of the second impinger bottle and through the deionized water. Five (5) ml of concentrated sulfuric acid was diluted with 50 ml of water and added to the sodium chlorite solution in the first impinger bottle to begin converting chlorite anion to chlorine dioxide. After 5 minutes, 20 ml of concentrated sulfuric acid was added and the solution in the first bubbler turned orange-yellow in color due to the presence of a high concentration of dissolved chlorine dioxide. Chlorine dioxide was stripped from the solution in the first impinger and transferred to the water in the second impinger by the flowing air. The concentration of molecular chlorine dioxide in the second impinger bottle solution was 90 mg/l after 2 minutes and 890 mg/l after 15 minutes (determined by iodometric titration). This solution was used as a standard solution for substantially pure chlorine dioxide.

Ion chromatography analysis of the standard solution showed that it contained a small amount of chlorite and chlorate anions in addition to chlorine dioxide. This is believed to be the result of slight disproportionation of chlorine dioxide to chlorous and chloric acids at the generally neutral pH of the standard solution. Consequently, the ratio of Chlorine Dioxide to chlorite anion of the standard solution was less than infinite.

Example 1

Three hundred (300) grams of synthetic Y zeolite (Si/Al=2.7) was ion exchanged with 1000 ml of ammonium sulfate (5 Wt. %) solution at 70° C. for 3 hours. After exchange, the solid material was filtered and washed with deionized water. This procedure was repeated twice more and then the washed ammonium form zeolite was dried at about 100° C. and calcined at 450° C. for 5 hours under flowing air to produce calcined HY zeolite.

Two hundred (200) grams of calcined HY zeolite was mixed with 27.5 grams of dried technical grade sodium chlorite in a glove bag at room temperature to produce a dried reactant mixture.

One (1) gram of the dried reactant mixture was placed in a Tyvek sachet and sealed. This sachet was then immersed in 500 ml of deionized water (pH 6.3) in a closed glass bottle. After 15 minutes, the solution developed a yellow color due to the release of chlorine dioxide from the sachet into the water and yellow color reached its maximum intensity about 2 hours immersion of the sachet into the water. The solution was then cooled to 5° C. before opening the bottle and 100 ml of solution was transferred to a 250 ml Pyrex beaker where the Total Concentration and the Chlorite Concentration were measured by iodometric titration. The concentration of free molecular chlorine dioxide in solution was 55 mg/l and it had a ratio of Chlorine Dioxide to chlorite anion of about 50. The pH of the solution was about 5.6.

The sodium content of the solution was measured by AAS and found to be substantially zero (ppb levels). The concentrations of chlorite and chlorate anions in solution were measured by ion chromatography, and the ratio between the chlorite and chlorate concentrations was the same as that in the Standard Solution, indicating that the chlorite and chlorate had probably resulted from the disproportionation of chlorine dioxide and were not contaminants produced by the sachet.

The procedure above was repeated with a larger sachet containing 10 grams of dried reactant mixture, and it produced a solution containing about 550 mg/l of chlorine dioxide and having a ratio of Chlorine Dioxide to chlorite anion of about 50.

Example 2

One hundred twenty (120) grams of calcined HY zeolite made as in Example 1 was mixed with 30 grams of dried technical grade sodium chlorite in a glove bag. One gram of this mixture was sealed in a Tyvek sachet and tested as described in Example 1. It yielded a solution containing about 85 mg/l of free molecular chlorine dioxide with a Chlorine Dioxide to chlorite anion ratio of about 40. Ten (10) grams of the mixture generated a concentration of about 880 mg/l of chlorine dioxide in solution.

Example 3

A. Six hundred twenty-five (625) grams of metakaolin microspheres were impregnated with 60 ml of concentrated sulfuric acid and 500 ml of water. The wet material was dried at 120° C. for 8 hours and crushed and sieved. The resultant dried acid treated metakaolin microspheres were crushed and screened to a size range of between about 44 to 74 microns in diameter.

B. Sixty-five (65) grams of anhydrous calcium chloride were mixed with the 625 grams of acid treated metakaolin microspheres and the mixture was dried at 200° C. for 3 hours. While still warm (nominally about 60° C.), the resultant dried mixture of calcium chloride and acid treated metakaolin microspheres was sealed in a glass jar and allowed to cool to room temperature.

C: Sixty (60) grams of dried technical grade sodium chlorite were mixed with the dried mixture of calcium chloride and acid treated metakaolin microspheres in a glove bag and the resultant reactant mixture was stored in a sealed glass jar.

D: Ten (10) grams of the reactant mixture were sealed in a Tyvek sachet and tested as in example 1. Yellow chlorine dioxide solution was generated within 10 minutes and the chlorine dioxide concentration was about 250 mg/l. The ratio of Chlorine Dioxide to chlorite anion was about 25.

Example 4

Fifty (50) grams of boric acid, 25 grams of anhydrous calcium chloride and 12.5 grams of technical grade sodium chlorite were dried at 100° C. for 1 hour separately. All three were cooled to room temperature in sealed bottles and mixed in a glove bag.

Five (5) grams of the mixture were sealed in a Tyvek sachet and tested as in Example 1, but the release time was only 10 minutes. The resultant yellow solution had a chlorine dioxide concentration of about 95 mg/l and a Chlorine Dioxide to chlorite anion ratio of about 50.

Example 5

Fifty (50) grams of citric acid were dried at 90° C. for 1 hour and cooled room temperature in a sealed container. Twenty (20) grams of anhydrous calcium chloride was dried at 200° C. for 1 hour and cooled to room temperature in a sealed container. The dried citric acid and calcium chloride were mixed with 12.5 grams of dried technical grade sodium chlorite in a glove bag to yield a reactant mixture.

Five (5) grams of the reactant mixture were sealed in a Tyvek sachet and tested as in Example 1. The resultant yellow solution had a chlorine dioxide concentration of about 165 mg/l and a Chlorine Dioxide to chlorite anion ratio of about 40 after 1 hour.

Example 6

Five hundred (500) grams of citric acid was dried at 90° C. for 3 hours and cooled to room temperature in a sealed container. Two hundred fifty (250) grams of anhydrous calcium chloride was dried at 250° C. for 3 hours and cooled to room temperature in a sealed container. The dried citric acid and dried calcium chloride were mixed with 250 grams of dried technical grade sodium chlorite in a glove bag to yield a reactant mixture.

One gram of the reactant mixture was loaded by hand into a Capsugel® brand gelatin capsule in a glove bag under a dry atmosphere. The capsule was tested as in Example 1 and it generated a solution having a Total Oxidant Concentration of about 110 mg/l within 15 minutes. The solution had a Chlorine Dioxide to chlorite anion ratio of about 0.1.

Example 7

One hundred (100) grams of sodium hydrogen sulfate was dried at 90° C. for 3 hours and cooled to room temperature in a sealed container. Fifty (50) grams of anhydrous calcium chloride was dried at 250° C. for 3 hours and cooled to room temperature in a sealed container. Similarly, 50 grams of sodium chlorite was also dried at 90° C. for 3 hours and cooled to room temperature in a sealed container. All three components were mixed in a glove bag.

One (1) gram of the material was placed in a Capsugel brand dissolvable capsule and tested as in Example 1. It generated a solution having a Total Oxidant Concentration of about 109 mg/l within about 15 minutes. The solution had a Chlorine Dioxide to chlorite anion ratio of about 0.1.

What is claimed is:

1. A device capable of producing an aqueous solution of chlorine dioxide when said device is placed into water, the device comprising a water-permeable membrane defining at least in part an enclosed space containing a direct mixture of at least one metal chlorite and at least one acid forming component, said acid forming component being selected from the group consisting of synthetic molecular sieves, acid ion exchange resins, acid treated clays and acid treated calcined clays, and wherein said metal chlorite and said acid forming component are such that they will react with each other in the presence of water but not in the substantial absence of water to produce chlorine dioxide, said membrane comprising a material which permits: (a) controlled passage of liquid water and/or water vapor into the enclosed space to thereby allow the metal chlorite and the acid forming component to react to produce chlorine dioxide and (b) passage of the so produced chlorine dioxide into a body of liquid water to produce the aqueous solution of chlorine dioxide.

2. The device of claim 1 wherein the membrane is substantially water insoluble.

3. The device of claim 1 wherein the metal chlorite is selected from the group consisting of alkali metal chlorites and alkaline earth metal chlorites.

4. The device of claim 1 wherein the metal chlorite is sodium chlorite.

5. The device of claim 1 wherein the synthetic molecular sieves are selected from the group consisting of synthetic zeolite Y, dealuminated Y, mordenite end ZSM-5.

6. The device of claim 1 wherein the acid forming component produces a pH below about 5 when mixed with water.

7. The device of claim 1 wherein the aqueous solution of chlorine dioxide has a pH from about 2 to about 10.

8. The device of claim 1 wherein the membrane is water softenable.

9. The device of claim 2 wherein the membrane material is made from a microporous nonwoven hydrophobic polymer.

10. The device of claim 9 wherein the microporous nonwoven hydrophobic polymer is selected from polyethylene and polytetrafluoroethylene.

11. The device of claim 1 wherein the membrane contains openings of sufficient size to enable the controlled passage of water into contact with the metal chlorite and the acid forming component, wherein the metal chlorite is in the form of a powder and the metal chlorite is mixed with the acid forming component in the enclosed space.

12. The device of claim 1 wherein the mixture is present in the form of tablets.

13. The device of claim 1 wherein the mixture is present in the form of powders.

14. The device of claim 1 wherein the mixture is present in the form of granules.

15. The device of claim 1 wherein the mixture is present in the form of pellets.

16. The device of claim 1 wherein the mixture is present in the form of agglomerates.

17. The device of claim 16 wherein the agglomerates are present as two types:
   (a) a first type at least one metal chlorite or a mixture of one or more metal chlorites and one or more non-acid forming additives; and
   (b) a second type comprising at least one acid forming component or a mixture of one or more acid forming components and one or more metal chlorite-free additives.

18. The device of claim 17 wherein the non-acid forming additives are selected from the group consisting of silica gel desiccant, paraffin wax tableting binder, sodium and sulfate filler and mixtures thereof.

19. The device of claim 17 wherein the metal chlorite-free additives are selected from the group consisting of ion exchangers, tableting binders, desiccants and mixtures thereof.

20. The device of claim 16 wherein the agglomerates have a particle size of at least 80 microns.

21. The device of claim 20 wherein the agglomerates have a particle size above about 500 microns.

22. The device of claim 21 wherein the agglomerates have a particle size above about 1,000 microns.

23. The device of claim 1, wherein the membrane comprises kraft paper.

24. The device of claim 1 capable of producing an aqueous solution comprising from about 0.5 ppm to about 200 ppm chlorine dioxide.

* * * * *